(12) United States Patent
Meier

(10) Patent No.: US 11,568,760 B1
(45) Date of Patent: Jan. 31, 2023

(54) AUGMENTED REALITY CALORIE COUNTER

(71) Applicant: Apple Inc., Cupertino, CA (US)

(72) Inventor: Peter Meier, Los Gatos, CA (US)

(73) Assignee: Apple Inc., Cupertino, CA (US)

( * ) Notice: Subject to any disclaimer, the term of this patent is extended or adjusted under 35 U.S.C. 154(b) by 1128 days.

(21) Appl. No.: 16/146,909

(22) Filed: Sep. 28, 2018

Related U.S. Application Data

(60) Provisional application No. 62/565,871, filed on Sep. 29, 2017.

(51) Int. Cl.
| | |
|---|---|
| *G06K 9/62* | (2022.01) |
| *G09B 19/00* | (2006.01) |
| *G01N 33/02* | (2006.01) |
| *G06N 20/00* | (2019.01) |
| *G06V 20/68* | (2022.01) |
| *G10L 25/48* | (2013.01) |

(52) U.S. Cl.
CPC ......... *G09B 19/0092* (2013.01); *G01N 33/02* (2013.01); *G06N 20/00* (2019.01); *G06V 20/68* (2022.01); *G06K 9/62* (2013.01); *G10L 25/48* (2013.01)

(58) Field of Classification Search
CPC .... G09B 19/0092; G01N 33/02; G06N 20/00; G06V 20/68; G06K 9/62; G10L 25/48
USPC ........................................................ 434/127
See application file for complete search history.

(56) References Cited

U.S. PATENT DOCUMENTS 5,263,491 A * 11/1993 Thornton ............. A61B 5/4866
600/587
2020/0152312 A1* 5/2020 Connor .................... A61B 5/11

* cited by examiner

*Primary Examiner* — Charlotte M Baker
(74) *Attorney, Agent, or Firm* — Blank Rome LLP

(57) ABSTRACT

Detecting a chewing noise from a user during a chewing session, triggering operation of a camera, obtaining image data capturing a food product, identifying the food product based on image data, determining a measurement of the chewing session, determining a volume of the food product based on the measurement of the chewing session, and determining a calorie intake based on the food product, the volume of the food product, and the measurement of the chewing session.

16 Claims, 5 Drawing Sheets

US 11,568,760 B1

AUGMENTED REALITY CALORIE COUNTER

BACKGROUND

This disclosure relates generally to the field of digital image processing, and more specifically to the field of calorie counting in an augmented reality device.

Many factors contribute to inaccurate calorie counting. For example, serving sizes may be difficult to measure while eating in a restaurant. The result is that people have inaccurate calorie counts, impairing weight loss, accurate drug dosages, and more. Purchasing and eating only from single serving packages to ensure an accurate calorie count is expensive and impractical, and leads to an excessive amount of packaging materials. Thus, what is needed is an improved determination of food consumption.

SUMMARY

In one embodiment, a method for improving determination of food consumption is described. A method for improving determination of food consumption includes detecting, by a microphone, a chewing noise from a user during a chewing session; in response to detecting the chewing noise, triggering operation of a camera; obtaining, by the camera, image data capturing a food product; identifying the food product based on image data; determining a measurement of the chewing session; determining a volume of the food product based on the measurement of the chewing session; and determining a calorie intake based on the food product, the volume of the food product, and the measurement of the chewing session.

In another embodiment, the method may be embodied in computer executable program code and stored in a non-transitory storage device. In yet another embodiment, the method may be implemented in an electronic device having image and sound capture capabilities.

DETAILED DESCRIPTION

Figure 1:
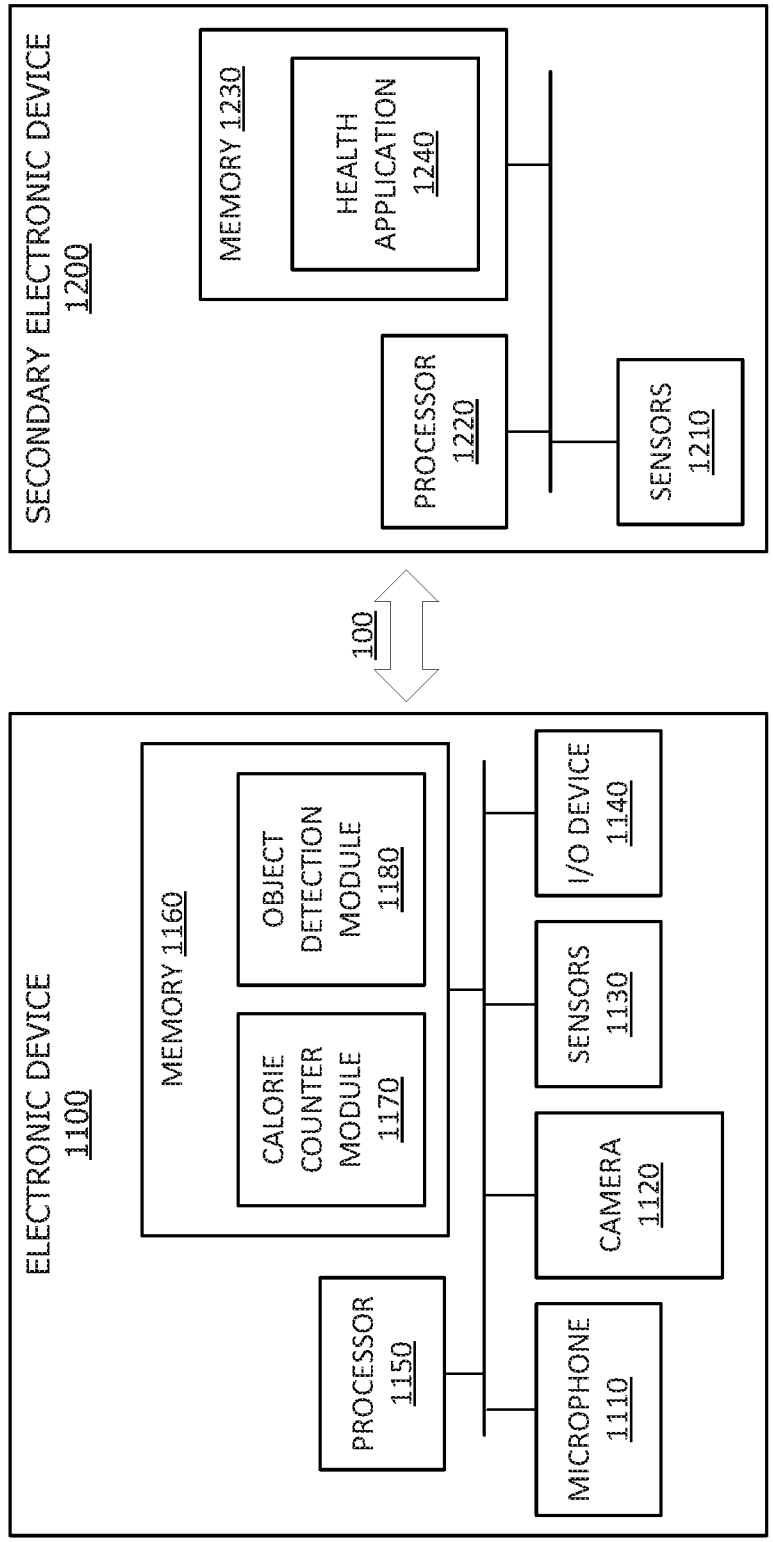
FIG. 1 shows, in block diagram form, a simplified electronic device and a secondary electronic device according to one or more embodiments.

This disclosure is directed to systems, methods, and computer readable media for improving determination of food consumption. In general, techniques are disclosed to improve determination of food consumption. According to one or more embodiments, improving determination of food consumption may allow a person to keep a more accurate calorie count.

According to one or more embodiments, a microphone may detect a chewing noise from a user during a chewing session. In response, a camera may take a picture of a food product. For example, the camera may take a picture of a sandwich and chips. The calorie intake may be determined by identifying the food product as a sandwich and chips, determining a measurement of the chewing session, and determining a volume of the sandwich and chips. In one or more embodiments, the determination of food consumption may be more accurate than traditional methods of calorie counting. Thus, when food consumption is determined, the user may keep a more accurate log of calorie intake.

In the following description, for purposes of explanation, numerous specific details are set forth in order to provide a thorough understanding of the disclosed concepts. As part of this description, some of this disclosure's drawings represent structures and devices in block diagram form in order to avoid obscuring the novel aspects of the disclosed embodiments. In this context, it should be understood that references to numbered drawing elements without associated identifiers (e.g., 100) refer to all instances of the drawing element with identifiers (e.g., 100a and 100b). Further, as part of this description, some of this disclosure's drawings may be provided in the form of a flow diagram. The boxes in any particular flow diagram may be presented in a particular order. However, it should be understood that the particular flow of any flow diagram is used only to exemplify one embodiment. In other embodiments, any of the various components depicted in the flow diagram may be deleted, or the components may be performed in a different order, or even concurrently. In addition, other embodiments may include additional steps not depicted as part of the flow diagram. The language used in this disclosure has been principally selected for readability and instructional purposes, and may not have been selected to delineate or circumscribe the disclosed subject matter. Reference in this disclosure to "one embodiment" or to "an embodiment" means that a particular feature, structure, or characteristic described in connection with the embodiment is included in at least one embodiment, and multiple references to "one embodiment" or to "an embodiment" should not be understood as necessarily all referring to the same embodiment or to different embodiments.

It should be appreciated that in the development of any actual implementation (as in any development project), numerous decisions must be made to achieve the developers' specific goals (e.g., compliance with system and business-related constraints), and that these goals will vary from one implementation to another. It will also be appreciated that such development efforts might be complex and time consuming, but would nevertheless be a routine undertaking for those of ordinary skill in the art of image capture having the benefit of this disclosure.

For purposes of this disclosure, the term "microphone" refers to a transducer that converts sound into an electrical signal. In one or more embodiments, the microphone may refer to any kind of microphone, such as a dynamic microphone, a condenser microphone, or a piezoelectric microphone. Further in one or more embodiments, the microphone may be an internal component of an electronic device or a separate external component connected to an electronic device at will by a user.

For purposes of this disclosure, the term "camera" refers to a lens assembly along with the sensor element and other circuitry utilized to capture an image. In one or more embodiments, the lens assembly may include multiple lenses. Further in one or more embodiments, the lens may be moved to various positions to capture images at multiple depths and, as a result, multiple points of focus. In one or more embodiments, the lens may refer to any kind of lens, such as a telescopic lens or a wide angle lens. As such, the lens assembly can mean a single optical element or multiple elements configured into a stack or other arrangement.

Referring to FIG. 1, a simplified block diagram of an electronic device 1100 is depicted, in accordance with one or more embodiments of the disclosure. Electronic device 1100 may be part of a multifunctional device, such as a mobile phone, tablet computer, personal digital assistant, portable music/video player, wearable device, or any other electronic device that includes a camera system and either a microphone system or an externally connected independent microphone system.

FIG. 1 shows, in block diagram form, an overall view of a system diagram capable of supporting improved determination of food consumption, according to one or more embodiments. Specifically, FIG. 1 depicts an electronic device 1100 that is a computer system. Electronic device 1100 may be connected to other network devices across a network, such as secondary electronic device 1200, mobile devices, tablet devices, desktop devices, as well as network storage devices such as servers and the like. Electronic device 1100 may also be connected to secondary electronic device 1200 via a wireless, or a wired connection. FIG. 1 shows connection 100 between electronic device 1100 and secondary electronic device 1200, which may be a network connection, a wired connection, or a Bluetooth connection, among others.

Electronic device 1100 may include a processor 1150. Processor 1150 may be a system-on-chip such as those found in mobile devices and include one or more central processing units (CPUs), dedicated graphics processing units (GPUs), or both. Further processor 1150 may include multiple processors of the same or different type. Electronic device 1100 may also include a memory 1160. Memory 1160 may include one or more different types of memory, which may be used for performing device functions in conjunction with processor 1150. For example, memory 1160 may include cache, ROM, and/or RAM. Memory 1160 may store various programming modules during execution, including calorie counter module 1170 and object detection module 1180. In one or more embodiments, memory 1160 may also include health application 1240.

Electronic device 1100 may include one or more microphones, such as microphone 1110. Microphone 1110 may include a diaphragm and an analog to digital converter. In one or more embodiments, microphone 1110 may detect a chewing noise from a user during a chewing session. For example, processor 1150 may obtain the audio data for the chewing session captured by microphone 1110 and determine frequency and amplitude data in the audio data. Processor 1150 may then detect the chewing noise based on the frequency and amplitude data.

Electronic device 1100 may also include one or more cameras, such as camera 1120. Camera 1120 may include an image sensor, a lens stack, and other components that may be used to capture images. For example, camera 1120 may be configured to capture images of an environment from the point of view of a user. In addition, camera 1120 may include multiple cameras, configured to capture images from different points of view. Electronic device 1100 may also include additional sensors 1130. For example, sensors 1130 may include a blood glucose monitor or a vibration sensor attuned to chewing vibrations.

In one or more embodiments, the electronic device 1100 may also include input/output (I/O) device 1140. I/O device 1140 may be any kind of input or output device, such as microphones for voice control input, speakers for audio data output, cameras for visual input, displays for visual data output, touch screens for tactile input, or any combination thereof. For example, I/O device 1140 may be any kind of display device, such as an LCD display, LED display, OLED display, or the like. Further, the display device may be a traditional display or a semi-opaque display, such as a heads up display or the like. Further, the display may be part of a head-mounted display, according to one or more embodiments.

Although electronic device 1100 is depicted as comprising the numerous components described above, in one or more embodiments, the various components may be distributed across multiple devices as part of a distributed system. Further, additional components may be used and some of the functionality of any of the components may be combined.

In one or more embodiments, calorie counter module 1170 is configured to determine the calorie intake of a user. For example, the calorie counter module 1170 may be used to determine a calorie intake based on an identified food product, the volume of the identified food product, and a measurement of a chewing session. The food product may be identified in any number of ways. For example, in one or more embodiments calorie counter module 1170 may work in conjunction with object detection module 1180 and camera 1120 to identify the food product. In one or more embodiments, calorie counter module 1170 may then determine a measurement of a chewing session in conjunction with at least microphone 1110, sensors 1130, or some combination thereof. Calorie counter module 1170 may then determine a volume of the food product using the measurement of the chewing session before determining a calorie intake. In one or more embodiments, calorie counter module 1170 may also determine a total daily calorie intake based at least in part on the determined calorie intake, compare the total daily calorie intake with a predetermined threshold, and present a notification based on the comparing through I/O device 1140.

In one or more embodiments, object detection module 1180 is configured to identify a food product based on image data capturing the food product. For example, in one or more embodiments object detection module 1180 may work in conjunction with camera 1120 to obtain image data capturing the food product and identify the food product using a machine learning algorithm. In one or more embodiments, object detection module 1180 may also obtain location information associated with the image data and identify the food product based at least in part on the location information. For example, location information associated with the image data may indicate a particular restaurant, prompting object detection module 1180 and processor 1150 to use the restaurant's menu to identify the food product.

FIG. 1 also shows secondary electronic device 1200 connected to electronic device 1100. Secondary electronic device 1200 may be a mobile device, a tablet, a smartwatch, goggles, or the like. In one or more embodiments, secondary electronic device 1200 comprises sensors 1210, processor 1220, and memory 1230. In one or more embodiments, sensors 1210 may include a blood glucose monitor or other sensors utilized to measure the effect of food on a body, such as blood glucose levels. Processor 1220 may be a system-on-chip such as those found in mobile devices and include one or more central processing units (CPUs), dedicated graphics processing units (GPUs), or both. Further processor 1220 may include multiple processors of the same or different type. Electronic device 1200 may also include a memory 1230. Memory 1230 may include one or more different types of memory, which may be used for storing computer readable code to perform device functions in conjunction with processor 1220. For example, memory 1230 may include cache, ROM, and/or RAM. Memory 1230 may store various programming modules during execution, including health application 1240.

In one or more embodiments, health application 1240 is configured to obtain a glucose measurement. For example, health application 1240 may work in conjunction with a blood glucose monitor included in sensors 1210 to obtain a blood sample and measure blood sugar. In one or more embodiments where health application 1240 is stored in memory 1160, health application may work in conjunction with a blood glucose monitor included in sensors 1130 to obtain and/or utilize a blood sample to measure blood glucose levels. As another example, sensor 1130 may obtain optical, electrical, or other data utilized to measure blood glucose levels.

Figure 2:
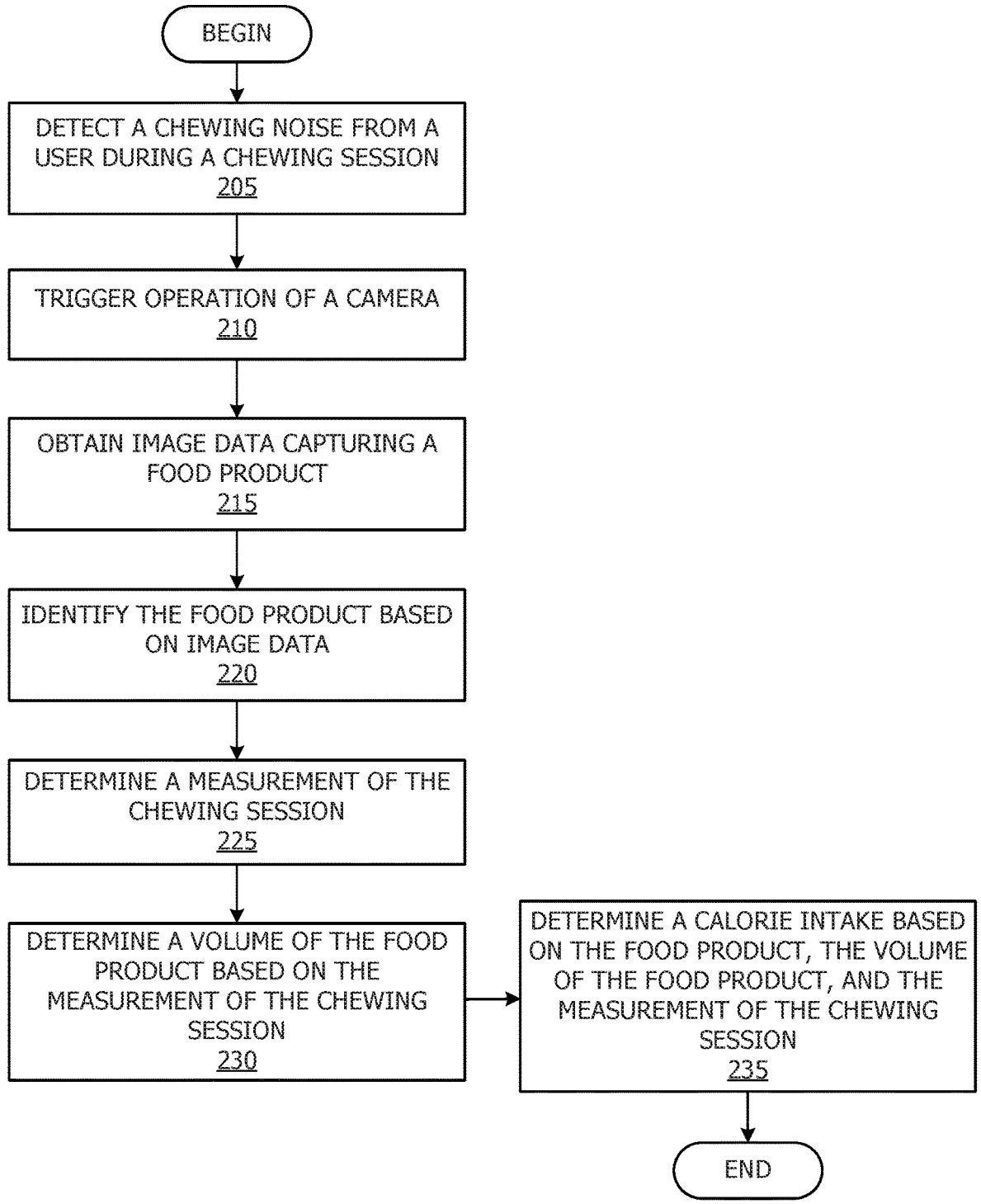
FIG. 2 shows, in flow chart form, an example method for improving determination of food consumption, according to one or more embodiments.

FIG. 2 shows, in flow chart form, a method for improving determination of food consumption. For purposes of explanation, the following steps will be described in the context of FIG. 1. However, it should be understood that the various actions may be taken by alternate components. In addition, the various actions may be performed in a different order. Further, some actions may be performed simultaneously, and some may not be required, or others may be added, according to various embodiments.

The flow chart begins at 205, where microphone 1110 detects a chewing noise from a user during a chewing session. In one or more embodiments, detecting the chewing noise may indicate the beginning of a chewing session. The flow chart continues at 210, where the calorie counter module 1170 triggers operation of camera 1120. According to one or more embodiments, the camera 1120 may be triggered in response to detecting the beginning of a chewing session, or otherwise based on data captured by the microphone. In one or more embodiments, triggering the operation of a camera may include powering on the camera 1120 or switching the camera 1120 from a low power mode to a high power mode. At 215, calorie counter module 1170 obtains image data capturing a food product from camera 1120. The image data may include a still image, a video stream, a series of frames, a live image, or the like. Further, in one or more embodiments, the image data may include location data.

The flow chart continues at 220, where the calorie counter module 1170 identifies the food product based on image data. In one or more embodiments, calorie counter module 1170 may work in conjunction with object detection module 1180 to identify the food product. For example, object detection module 1180 may use a machine learning algorithm to identify the food product, as discussed previously. In one or more embodiments, calorie counter module 1170 may also obtain location information associated with the image data and identify the food product based at least in part on the location information. The location information may be obtained, for example, based on GPS information, network connection information, and the like. Location information may include, for example, a physical location of the electronic device, and/or contextual information, such as whether the device is in a particular restaurant or other establishment, or is at home, or the like.

In one or more embodiments, the calorie counter module 1170 may obtain depth information from the electronic device 1100, or other device, regarding the food product. For example, electronic device 1100 may include a depth camera or other type of sensor or set of sensors which may be used to determine depth. According to one or more embodiments, the object detection module 1180 may determine characteristics of the food product based on the depth information. For example, by determining a detected depth or set of depths of the food product, and an apparent size from the perspective of the electronic device 1100, an estimated size and/or volume of the food product may be determined.

In one or more embodiments, the electronic device 1100 may include a microphone 1100 which may capture a recording of the user's speech. In one or more embodiments, recorded conversation or other description may be utilized to refine the object detection to identify the food product. As an example, the object detection module 1180 may register the user saying "this chicken is good!" and thus determine that the food product includes chicken. In one or more embodiments, the voice of the user may provide contextual clues regarding the food product by which the object detection module 1180 can better identify the food product. As an example, a user may say, "Which dressing would you like?" The object detection module may detect the word "dressing" as being related to a salad, for example, or a holiday meal that may include multiple kinds of dressings.

According to one or more embodiments, the object detection module 1180 may record a food preparation process. As a simple example, the object detection module may better understand the components of a sandwich by tracking the ingredients of the sandwich as it is being constructed. The electronic device 1100 may then store characteristics of the sandwich in a food bank, in local storage and/or in remote storage, such as network storage.

At 225, calorie counter module 1170 determines a measurement of the chewing session. Calorie counter module 1170 may work in conjunction with the microphone 1110, sensors 1130, or some combination thereof. In one or more embodiments, a measurement of the chewing session may be a length of time, a number of times a user swallowed, or the like. For example, microphone 1110 may be used to establish a time chewing began and a time chewing stopped such that calorie counter module 1170 may determine a length of time of the chewing session. Further, in another embodiment, sensors 1130 may comprise a vibrational sensor attached to a user's throat to detect when the user swallows. Calorie counter module 1170 may use the detection of each time the user swallows to count the number of times the user swallowed in the chewing session. In addition, in one or more embodiments, characteristics of the chewing session may be analyzed to determine other characteristics of the food, such as a volume of food in the mouth during the chewing session, a texture of the food, and the like.

The flow chart continues at 230, where the calorie counter module 1170 determines a volume of the food product based on the measurement of the chewing session. In order to determine the volume of the food product based on the measurement of the chewing session, in one or more embodiments calorie counter module 1170 may estimate the volume of the food product per bite and multiply that estimated volume per bite by the number of times the user swallowed in the chewing session. In one or more embodiments, the calorie counter module 1170 may estimate a rate of intake of the food product and multiply by the length of time of the chewing session. In one or more embodiments, the user may input the volume of food per bite or the rate of intake of the food product via I/O device 1140 for the calorie counter module 1170 to use. In one or more embodiments, the volume of the food consumed may additionally, or alternatively, be determined based on a change in the appearance of food in front of the user. For example, the food product may be visually tracked using depth sensors, and the change in volume of food product in front of the user may be determined based on the determined size of the food product. As an example, the electronic device 1100 may utilize simultaneous localization and mapping ("SLAM") techniques to monitor the change in volume of food in front of the user. Further, in one or more embodiments, the volume consumed may additionally, or alternatively, be determined based on comparative characteristics of other items in front of the user. As an example, the food or drink may be on or in a plate or cup. Thus, if a size of a particular plate or cup is known or determinable, then an original volume or amount of food or drink may be determined based on the relative size of the vessel (e.g., the plate or cup). Further, as the volume of food changes, the comparative size of the plate or cup will change (e.g., the viewable surface of the plate or cup will increase). Accordingly, the amount of food or drink consumed may be estimated, at least in part, based on the changed viewable portion of the vessel.

At 235, calorie counter module 1170 determines a calorie intake based on the food product, the volume of the food product, and the measurement of the chewing session. In order to determine a calorie intake, in one or more embodiments calorie counter module 1170 may determine nutritional information for the food product and use the nutritional information for the food product in conjunction with the volume of the food product to determine a calorie intake.

As discussed previously, in one or more embodiments, the calorie counter module 1170 may further determine a total daily calorie intake based at least in part on the calorie intake, compare the total daily calorie intake with a predetermined threshold, and present a notification based on the comparing. Determining a total daily calorie intake may require calorie counter module 1170 to keep a log of all determined calorie intakes for a predetermined length of time. In one or more embodiments, the predetermined threshold may be set by the user via I/O device 1140. For example, the user may speak the threshold as part of a voice command or input the threshold via a touchscreen or keyboard. Calorie counter module 1170 may present the notification as an audio, tactile, or visual notification.

Figure 3:
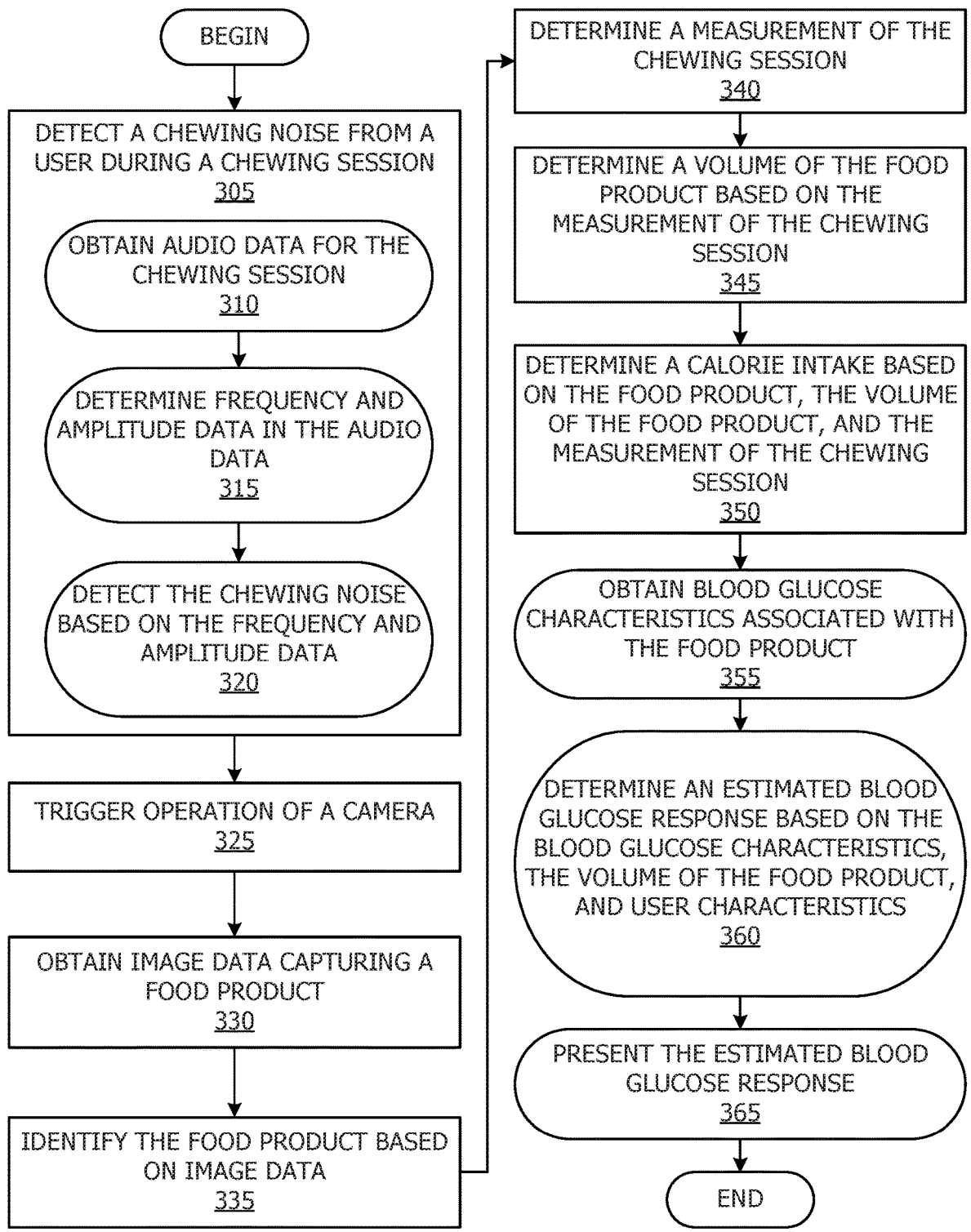
FIG. 3 shows, in flow chart form, a further example method for improving determination of food consumption including estimation of blood glucose response, according to one or more embodiments.

FIG. 3 shows, in flow chart form, a method for improving determination of food consumption, according to one or more embodiments. In one or more embodiments, the certain actions take place as part of detecting a chewing noise from a user during a chewing session while other actions take place as part of identifying the food product. Still other actions comprise additional functionality. However, the various actions may take place in other locations within the flow chart of FIG. 2. For purposes of explanation, the following steps will be described in the context of FIG. 1. However, it should be understood that the various actions may be taken by alternate components. In addition, the various actions may be performed in a different order. Further, some actions may be performed simultaneously, and some may not be required, or others may be added.

The flow chart begins at 305 and the microphone 1110 detects a chewing noise from a user during a chewing session. Detecting a chewing noise from a user during a chewing session may optionally further comprise steps 310, 315, and 320. At 310, the calorie counter module 1170 obtains audio data for the chewing session from microphone 1110. Next, the calorie counter module 1170 determines frequency and amplitude data in the audio data at 315. Detecting a chewing noise from a user during a chewing session may end at step 320, where the calorie counter module 1170 detects the chewing noise based on the frequency and amplitude data. For example, in one or more embodiments, the electronic device 1100 may be calibrated for a particular user's chew, or a generic user's chew. Thus, a user's chew may be identified based on frequency and amplitude data.

At 325, the calorie counter module 1170 triggers operation of camera 1120. As described above, the detection of the beginning of the chewing session may trigger operation of the camera, according to one or more embodiments. Further, in one or more embodiments, operation of the camera may be triggered in other ways, such as by detecting a food item in the field of view. Further, as described above, triggering operation of a camera may include powering on a camera, or switching a camera from a low power mode to a high power mode. Thus, for example, the food item may be detected in a low power mode, and the camera is switched from the lower power mode to a high power mode to obtain better image data. The flow chart continues at 330, where calorie counter module 1170 obtains image data capturing a food product from camera 1120.

At 335, calorie counter module 1170 identifies the food product based on image data. Recall calorie counter module 1170 may work in conjunction with object detection module 1180 to identify the food product. In one or more embodiments, a machine learning algorithm is used to identify the food product. In one or more embodiments, the calorie counter module 1170 may estimate the food product based on the frequency and amplitude data determined from the audio data in 315. The food product's identification may be further based on or confirmed by estimating the food product. Further, in one or more embodiments calorie counter module 1170 may obtain location information associated with the image data and identify the food product based on the location information. As discussed previously, the location information may be utilized to identify a restaurant such that a calorie counter module 1170 may base the food product identification on the restaurant's menu. Further, the location information may be used to distinguish between a commercial and residential location so as to better determine whether an identified food product is homemade or commercially prepared.

The flow chart continues at 340, where calorie counter module 1170 determines a measurement of the chewing session. Recall the measurement of the chewing session may include a length of time or a number of swallows. At 345, calorie counter module 1170 determines a volume of the food product based on the measurement of the chewing session. As discussed previously, in one or more embodiments the volume of the food product may be determined based on the estimated volume of food product per bite and the number of swallows or an estimated rate of intake of the food product and the length of time of the chewing session. Calorie counter module 1170 may estimate the volume of food product per bite or the rate of intake of the food product or the user may input values.

At 350, calorie counter module 1170 determines a calorie intake based on the food product, the volume of the food product, and the measurement of the chewing session. As discussed previously, in one or more embodiments, the calorie counter module 1170 may determine nutritional information for the food product and use the nutritional information for the food product in conjunction with the volume of the food product to determine a calorie intake. Recall calorie counter module 1170 may also determine a total daily calorie intake based at least in part on the calorie intake, compare the total daily calorie intake with a predetermined threshold, and present a notification based on the comparing. Determining a total daily calorie intake may involve calorie counter module 1170 to keep a log of all determined calorie intakes for a predetermined length of time. Alternatively, calorie counter module 1170 may interface with a diet journal or other application utilized to track daily caloric intake. In one or more embodiments, the predetermined threshold may be set by the user via I/O device 1140. For example, the user may speak the threshold as part of a voice command or input the threshold via a touchscreen or keyboard. Calorie counter module 1170 may present the notification as an audio, tactile, or visual notification.

The flow chart continues with 355, where calorie counter module 1170 obtains blood glucose characteristics associated with the food product. In one or more embodiments, calorie counter module 1170 may obtain blood glucose characteristics as part of the nutritional information for the food product. In one or more embodiments, calorie counter module 1170 may obtain blood glucose characteristics from health application 1240. Note that health application 1240 may be stored in memory 1160 of electronic device 1100 or memory 1230 of secondary electronic device 1200. Further, in one or more embodiments obtaining blood glucose characteristics may include obtaining historic blood glucose measurement data associated with the food product and one or more additional users. For example, the blood glucose characteristics may utilize an anonymized version of additional user blood glucose characteristics to glean potential effects from a particular user consuming certain food products.

At 360, calorie counter module 1170 determines an estimated blood glucose response based on the blood glucose characteristics, the volume of the food product, and user characteristics. In one or more embodiments, user characteristics may include the user's past recorded glucose responses to the food product. Further, in one or more embodiments, determining an estimated blood glucose response is further based on context information for the user, where context information may include at least time of day, temperature, sleep patterns, location, or combinations thereof.

The flow chart continues with 365, where calorie counter module 1170 presents the estimated blood glucose response. In one or more embodiments, calorie counter module 1170 may present the estimated blood glucose response as an audio, tactile, or visual notification. For example, the estimated blood glucose response may be read out to the user or shown on a display using I/O device 1140. Further, if the estimated blood glucose response exceeds a predetermined threshold, I/O device 1140 may vibrate electronic device 1100, or otherwise present feedback to the user.

Calorie counter module 1170 may further obtain a blood glucose measurement in response to determining the volume of food product, compare the blood glucose measurement to the estimated blood glucose response, and modify the user characteristics based on the comparing. Calorie counter module 1170 may obtain a blood glucose measurement from a blood glucose monitor contained in sensors 1130 in electronic device 1100 or in sensors 1210 in electronic device 1200. In one or more embodiments, modifying the user characteristics based on the comparing may include updating a history of the user's past blood glucose responses to the food product.

Figure 4:
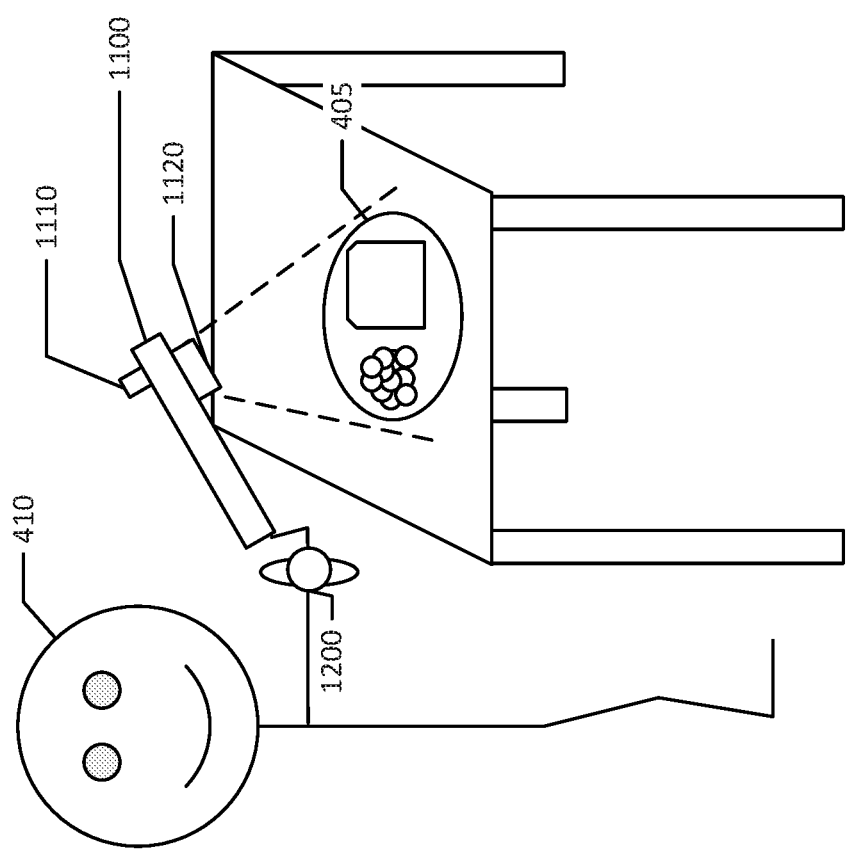
FIG. 4 shows, in system diagram form, an example setup of using an electronic device to improve determination of food consumption in conjunction with a secondary electronic device, according to one or more embodiments.

Referring now to FIG. 4, a system diagram is shown for an example setup for improving determination of food consumption, according to one or more embodiments. FIG. 4 shows a user 410 utilizing an electronic device 1100 to determine food consumption according to one or more embodiments. Electronic device 1100 uses camera 1120 to obtain image data of food product 405. Electronic device 1100 also uses microphone 1110 to detect a chewing noise from user 410. Electronic device 1100 is connected to secondary electronic device 1200, here a smartwatch, via Bluetooth. In this embodiment, secondary electronic device 1200 contains health application 1240.

In one or more embodiments, the history of food consumption may be stored locally or remotely, for example in network storage. Further, consumption history may also be stored, such as volume of food products consumed, caloric intake, and the like. In one or more embodiments, the system may also be used for meal planning. As an example, in response to determining that a time for a particular meal is approaching or has arrived, the system may present food options. The food options may be determined, for example, based on geographic data. As an example, GPS data may be used to locate nearby restaurants, and the historic data regarding food consumption may be utilized to identify food options available nearby. Further, in one or more embodiments, the food options may be presented in an order that is determined, for example, by historic caloric intake for a particular meal or the like.

Figure 5:
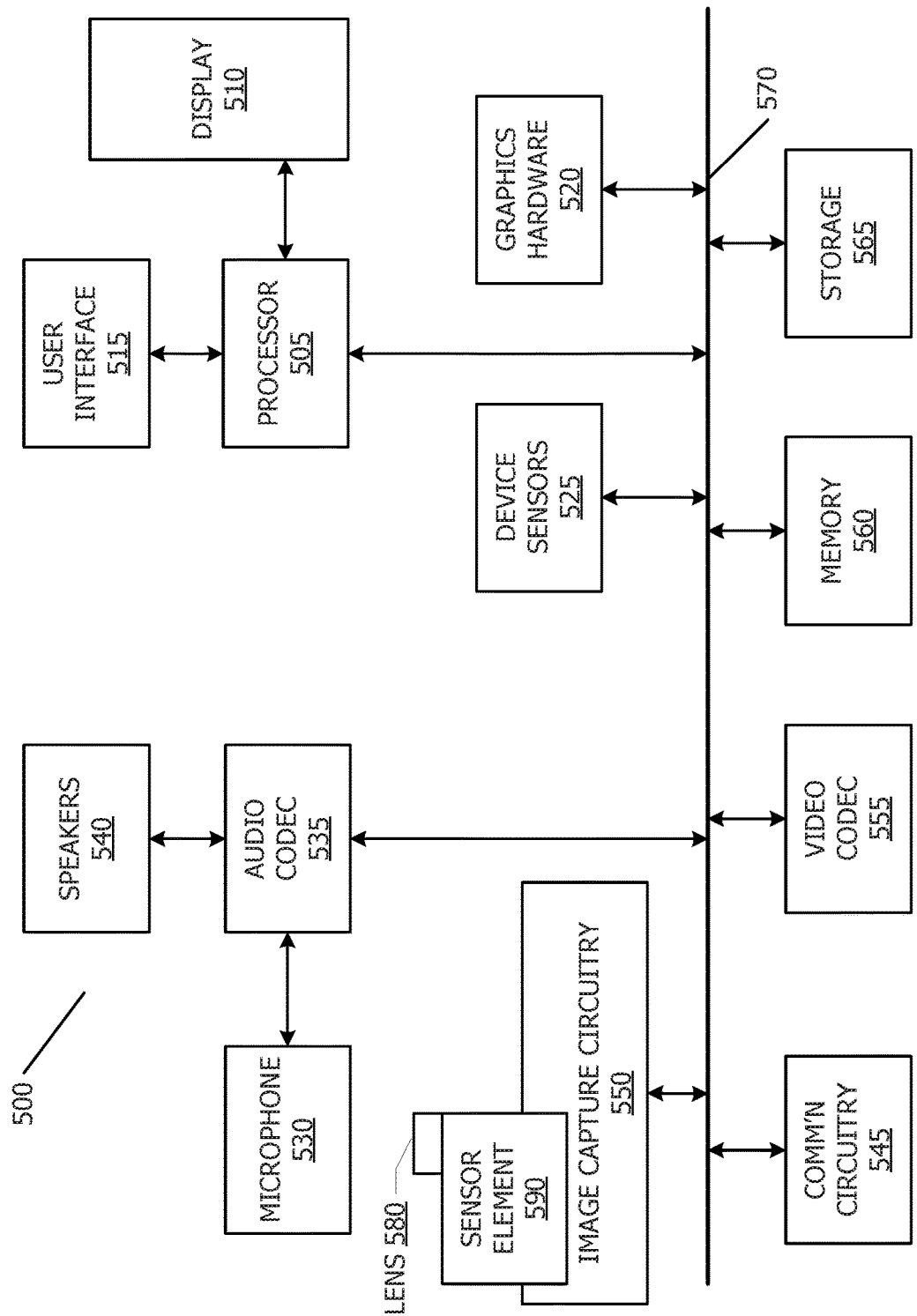
FIG. 5 shows, in block diagram form, a simplified multifunctional electronic device according to one or more embodiments.

Referring now to FIG. 5, a simplified functional block diagram of illustrative multifunction device 500 is shown according to one embodiment. Multifunction electronic device 500 may include processor 505, display 510, user interface 515, graphics hardware 520, device sensors 525 (e.g., proximity sensor/ambient light sensor, accelerometer and/or gyroscope), microphone 530, audio codec(s) 535, speaker(s) 540, communications circuitry 545, digital image capture circuitry 550, video codec(s) 555 (e.g., in support of digital image capture unit 550), memory 560, storage device 565, and communications bus 570. Multifunction electronic device 500 may be, for example, a personal electronic device such as a personal digital assistant (PDA), mobile telephone, or a tablet computer.

Processor 505 may execute instructions necessary to carry out or control the operation of many functions performed by device 500 (e.g., such as the determination of a calorie intake or estimated blood glucose response as disclosed herein). Processor 505 may, for instance, drive display 510 and receive user input from user interface 515. User interface 515 may allow a user to interact with device 500. For example, user interface 515 can take a variety of forms, such as a button, keypad, dial, a click wheel, keyboard, display screen and/or a touch screen. Processor 505 may also, for example, be a system-on-chip such as those found in mobile devices and include a dedicated graphics processing unit (GPU). Processor 505 may be based on reduced instruction-set computer (RISC) or complex instruction-set computer (CISC) architectures or any other suitable architecture and may include one or more processing cores. Graphics hardware 520 may be special purpose computational hardware for processing graphics and/or assisting processor 505 to process graphics information. In one embodiment, graphics hardware 520 may include a programmable GPU.

Image capture circuitry 550 may include lens 580. Lens assembly may have an associated sensor element 590. Image capture circuitry 550 may capture still and/or video images. Output from image capture circuitry 550 may be processed, at least in part, by video codec(s) 555 and/or processor 505 and/or graphics hardware 520, and/or a dedicated image processing unit or pipeline incorporated within circuitry 555. Images so captured may be stored in memory 560 and/or storage 565.

Sensor and camera circuitry 550 may capture still and video images that may be processed in accordance with this disclosure, at least in part, by video codec(s) 555 and/or processor 505 and/or graphics hardware 520, and/or a dedicated image processing unit incorporated within circuitry 550. Images so captured may be stored in memory 560 and/or storage 565. Microphone 530 may capture audio recordings that may be processed in accordance with this disclosure, at least in part, by audio codec(s) 535 and/or processor 505. Audio recordings so captured may be stored in memory 560 and/or storage 565.

Memory 560 may include one or more different types of media used by processor 505 and graphics hardware 520 to perform device functions. For example, memory 560 may include memory cache, read-only memory (ROM), and/or random access memory (RAM). Storage 565 may store media (e.g., audio, image and video files), computer program instructions or software, preference information, device profile information, and any other suitable data. Storage 565 may include one more non-transitory storage mediums including, for example, magnetic disks (fixed, floppy, and removable) and tape, optical media such as CD-ROMs and digital video disks (DVDs), and semiconductor memory devices such as Electrically Programmable Read-Only Memory (EPROM), and Electrically Erasable Programmable Read-Only Memory (EEPROM). Memory 560 and storage 565 may be used to tangibly retain computer program instructions or code organized into one or more modules and written in any desired computer programming language. When executed by, for example, processor 505 such computer program code may implement one or more of the methods described herein.

As described above, one aspect of the present technology is the gathering and use of data available from various sources to improve the delivery to users of nutritional or caloric intake. The present disclosure contemplates that in some instances, this gathered data may include personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver targeted content that is of greater interest to the user. Accordingly, use of such personal information data enables users to calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

The scope of the disclosed subject matter should be determined with reference to the appended claims, along with the full scope of equivalents to which such claims are entitled. In the appended claims, the terms "including" and "in which" are used as the plain-English equivalents of the respective terms "comprising" and "wherein."

The invention claimed is:

1. A method for improving determination of food consumption, comprising:
    detecting, by a microphone, a chewing noise from a user during a chewing session, wherein detecting the chewing noise comprises:
        obtaining audio data for the chewing session captured by the microphone;
        determining frequency and amplitude data in the audio data; and
        detecting the chewing noise based on the frequency and amplitude data; and
    in response to detecting the chewing noise, triggering operation of a camera;
    obtaining, by the camera, image data capturing a food product;
    identifying the food product based on the image data and the audio data, wherein the food product is identified using both the frequency and amplitude data and the image data;
    determining a measurement of the chewing session;
    determining a volume of the food product based on the measurement of the chewing session; and
    determining a calorie intake based on the food product, the volume of the food product, and the measurement of the chewing session.

2. The method of claim 1, wherein identifying the food product based on the image data comprises:
obtaining location information associated with the image data; and
identifying the food product based on the location information.

3. The method of claim 1, further comprising:
determining a total daily calorie intake based at least in part on the calorie intake;
comparing the total daily calorie intake with a predetermined threshold; and
presenting a notification based on the comparing.

4. The method of claim 1, wherein identifying the food product is further based on estimating the food product.

5. The method of claim 1, wherein identifying the food product based on the image data comprises utilizing a machine learning algorithm to identify the food product.

6. A system, comprising:
one or more microphones;
one or more cameras;
one or more processors; and
a memory coupled to the one or more processors and comprising instructions executable by the one or more processors to cause the system to:
detect, by the one or more microphones, a chewing noise from a user during a chewing session, wherein, to detect the chewing noise, instructions executable by the one or more processors further cause the system to:
obtain audio data for the chewing session captured by the microphone;
determine frequency and amplitude data in the audio data; and
detect the chewing noise based on the frequency and amplitude data; and
trigger operation of the one or more cameras in response to detecting the chewing noise;
obtain an image data capturing a food product;
identify the food product based on the image data and the audio data, wherein the food product is identified using both the frequency and amplitude data and the image data;
determine a measurement of the chewing session;
determine a volume of the food product based on the measurement of the chewing session; and
determine a calorie intake based on the food product, the volume of the food product, and the measurement of the chewing session.

7. The system of claim 6, wherein identifying the food product based on the image data comprises:
obtaining location information associated with the image data; and
identifying the food product based on the location information.

8. The system of claim 6, further comprising:
determining a total daily calorie intake based at least in part on the calorie intake;
comparing the total daily calorie intake with a predetermined threshold; and
presenting a notification based on the comparing.

9. The system of claim 6, further comprising:
obtaining blood glucose characteristics associated with the food product;
determining an estimated blood glucose response based on the blood glucose characteristics, the volume of the food product, and user characteristics; and
presenting the estimated blood glucose response.

10. The system of claim 9, further comprising:
obtaining a blood glucose measurement in response to determining the volume of food product;
comparing the blood glucose measurement to the estimated blood glucose response; and
modifying the user characteristics based on the comparing.

11. The system of claim 9, wherein determining the estimated blood glucose response is further based on context information for the user.

12. The system of claim 9, wherein obtaining blood glucose characteristics comprises obtaining historic blood glucose measurement data associated with the food product and one or more additional users.

13. The system of claim 9, wherein identifying the food product based on the image data comprises utilizing a machine learning algorithm to identify the food product.

14. A non-transitory machine readable medium comprising instructions executable by one or more processors to:
detect, by a microphone, a chewing noise from a user during a chewing session, wherein, to detect the chewing noise:
obtain audio data for the chewing session captured by the microphone;
determine frequency and amplitude data in the audio data; and
detect the chewing noise based on the frequency and amplitude data; and;
trigger operation of a camera in response to detecting the chewing noise;
obtain an image data capturing a food product;
identify the food product based on the image data and the audio data, wherein the food product is identified using both the frequency and amplitude data and the image data;
determine a measurement of the chewing session;
determine a volume of the food product based on the measurement of the chewing session; and
determine a calorie intake based on the food product, the volume of the food product, and the measurement of the chewing session.

15. The non-transitory machine readable medium of claim 14, wherein the instructions to identify the food product further comprise instructions to estimate the food product.

16. The non-transitory machine readable medium of claim 14, further comprising instructions to:
obtain blood glucose characteristics associated with the food product;
determine an estimated blood glucose response based on the blood glucose characteristics, the volume of the food product, and user characteristics; and
present the estimated blood glucose response.

* * * * *